United States Patent [19]

Dolzine et al.

[11] Patent Number: 5,292,307
[45] Date of Patent: Mar. 8, 1994

[54] DISPENSING PACKAGE FOR UNIT DOSAGE

[76] Inventors: Theodore W. Dolzine, 412 Rock Run Pl., Havre de Grace, Md. 21078; Steven I. Baskin, 1412 Cherokee La., Bel Air, Md. 21015

[21] Appl. No.: 945,671
[22] Filed: Sep. 16, 1992
[51] Int. Cl.⁵ .......................................... A6MN 31/00
[52] U.S. Cl. ............................................. 604/54; 604/59
[58] Field of Search .................. 604/54, 57, 59–63, 604/111; 222/78, 322, 325, 343, 510; 221/79, 87, 88, 209, 197, 270, 268

[56] References Cited

U.S. PATENT DOCUMENTS

| | | | |
|---|---|---|---|
| 2,513,014 | 6/1950 | Fields | 604/60 |
| 2,712,315 | 7/1955 | Rice | 604/60 |
| 2,718,299 | 9/1955 | Atwater et al. | 206/42 |
| 3,893,578 | 7/1975 | Melton, Jr. et al. | 214/305 |
| 4,074,806 | 2/1978 | Ardito | 221/87 X |
| 4,078,660 | 3/1978 | Lerro | 206/530 |
| 4,166,555 | 9/1979 | Cheetham | 222/365 |
| 4,300,678 | 11/1981 | Gyure et al. | 604/111 |
| 4,428,709 | 1/1984 | Peters | 414/412 |
| 4,474,308 | 10/1984 | Bergeron | 604/59 X |
| 4,733,707 | 3/1988 | Haber | 221/8 |
| 4,905,866 | 3/1990 | Bartell et al. | 221/88 X |
| 4,909,414 | 3/1990 | Heath | 221/25 |
| 5,009,561 | 4/1991 | Lombardino et al. | 414/412 |
| 5,019,125 | 5/1991 | Rebne et al. | 206/532 |
| 5,038,968 | 8/1991 | Albetski | |

FOREIGN PATENT DOCUMENTS

| | | | |
|---|---|---|---|
| 0431953 | 7/1926 | Fed. Rep. of Germany | 604/59 |
| 0252587 | 6/1926 | United Kingdom | 604/60 |

*Primary Examiner*—C. Fred Rosenbaum
*Assistant Examiner*—Frank Wilkens, III
*Attorney, Agent, or Firm*—Dann, Dorfman, Herrell and Skillman

[57] ABSTRACT

A unit dosage, packaged for direct administration into a body cavity, is encapsulated in a packet between a pair of leaves of foil. The leaves are sealed to each other about their peripheries. The packet is packaged with a tubular injector having a longitudinal bore extending from the head end of the injector to the tail end. The packet is positioned in the bore adjacent the head end by a annular support member having a central opening in registry with the bore. A plunger is mounted in the bore and has a head adapted to slide in the bore and a tail projecting out of the tail end of the tubular injector, and the tail end of the plunger is used to displace the head of the plunger through the packet, through the opening in the annular support, and beyond the head end of the tubular injector. The head of the plunger is provided with a beveled surface along one side.

13 Claims, 1 Drawing Sheet

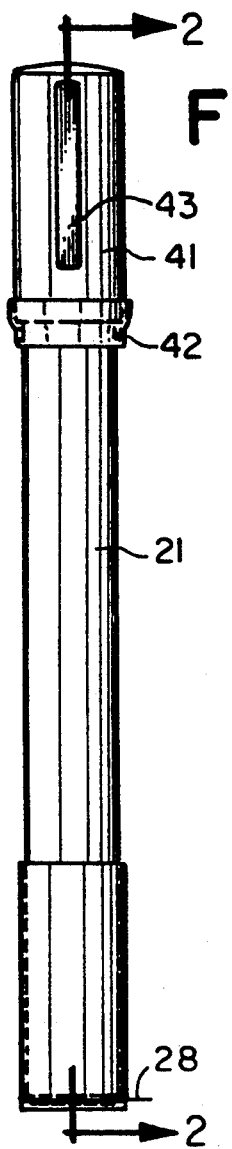
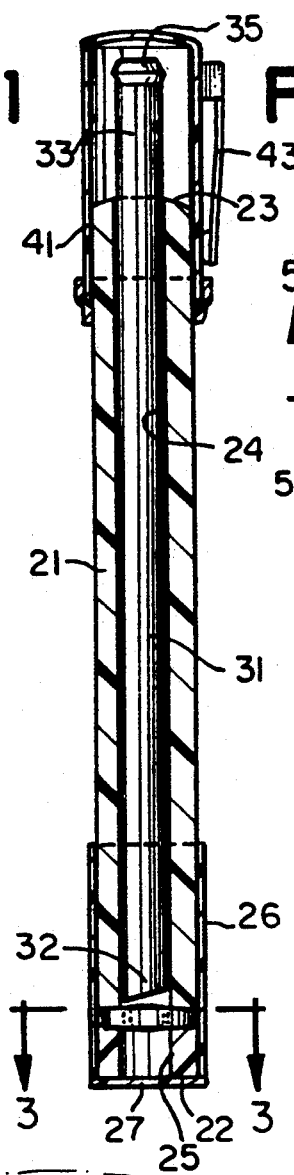
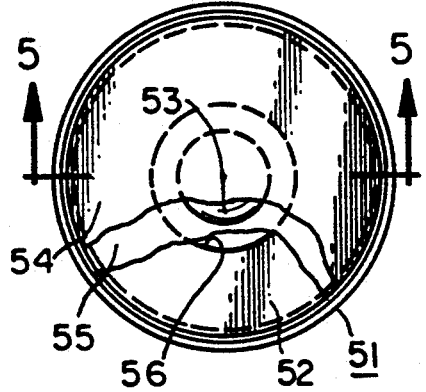
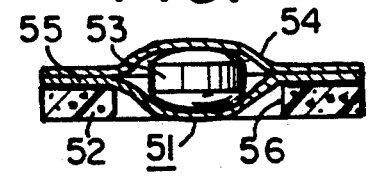
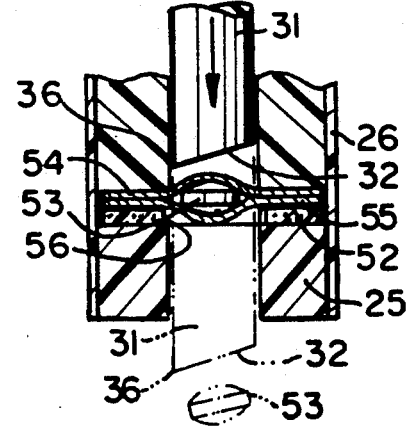
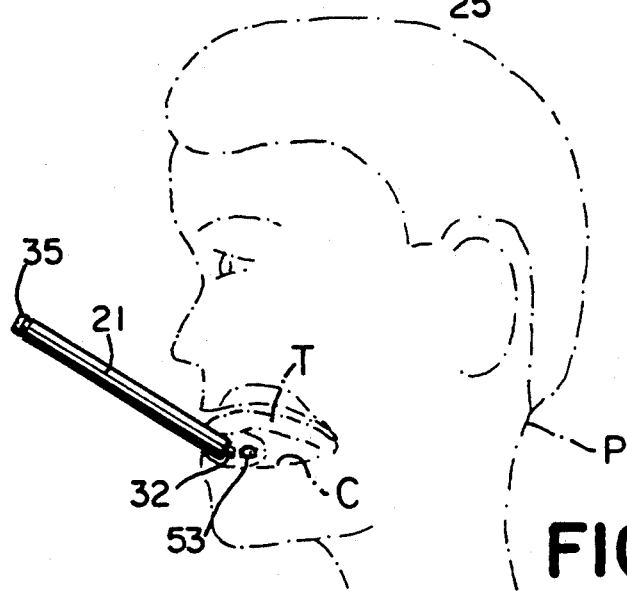

DISPENSING PACKAGE FOR UNIT DOSAGE

FIELD OF THE INVENTION

The present invention relates to a package which may be used to dispense unit dosages of medication, and a method of using the same, and is particularly applicable to dispensing medication which should be deposited in a localized area within a body cavity. The invention has particular applicability to the administration of a vasodilator, such as nitroglycerine, sublingually, and may be used to insert a variety of medications buccally or vaginally.

BACKGROUND OF THE INVENTION

Patients who are subject to angina attacks frequently carry a small supply of nitroglycerine tablets or other vasodilators to relieve the angina attack. In the case of severe attacks, the pain occasioned by such attacks may impair the patient's ability to open the medicine bottle, pull out the cotton, and select a tablet for placement under the tongue so as to relieve the attack. In the absence of such relief, there is a high risk of mortality. In order to render the medication more readily available, patients may transfer one or two dosages of the medication to a smaller container which renders the medication dosages more accessible than the standard medicine bottle. However, the transfer of the medication from the standard medicine bottle into the separate container may introduce contamination, and if the medication is not used for a period of time, the medication may be subject to degradation due to the ambient conditions in an around the smaller container. Furthermore, there is a risk that the supply of medication in the container may be depleted and may not be replenished before the next attack occurs.

SUMMARY OF THE INVENTION

With forgoing in mind, the present invention provides a package for a unit dosage of medication which is designed for a one-time use and disposal. The package is designed to facilitate the administration of the dosage sublingually, even when the person administering the dosage is somewhat impaired.

The package of the present invention encapsulates the medication dosage in a sealed packet so as to preserve the potency of the medication without degradation due to ambient conditions.

While the package of the present invention is designed primarily for use for self-administration by the patient, it is also effective for use by healthcare professionals, e.g., nurses, paramedics, physicians, as well as by untrained companions with a minimum of instruction.

Specifically, the present invention provides a dispensing package for a unit dosage of medicine having an elongated injector tube which may be inserted into the mouth or other body cavity so as to deposit the medication in a desired site within the cavity. The tubular injector of the present invention is provided with a receptacle for receiving an encapsulated packet of a unit dosage of the medication and then the packet is supported in the injector by an annular ring. A plunger is provided in the tubular injector to cooperate with the annular ring to first open the sealed packet and then express the medication from within the packet through the support ring and directly into the site for administration of the medication within the body cavity.

BRIEF DESCRIPTION OF THE DRAWINGS

The objects of the invention are more fully set forth hereinafter with reference to the accompanying drawings, wherein:

FIG. 1 is a front elevational view of a dispensing package made in accordance with the present invention;

FIG. 2 is a sectional view taken on the line 2—2 of FIG. 1;

FIG. 3 is a sectional view taken on line 3—3 of FIG. 2 with portions of the dosage packet broken away to illustrate its composition;

FIG. 4 is a sectional view through the packet assembly prior to mounting in the injector tube of the present invention;

FIG. 5 is a fragmentary sectional view taken on the line 5—5 of FIG. 3 showing the operation of the dispensing packaging; and FIG. 6 is a thumbnail sketch showing the use of the device to administer a sublingual dose of medication.

DESCRIPTION OF THE PREFERRED EMBODIMENT

Referring now to FIGS. 1 and 2, the illustrated dispensing package of the present invention comprises an elongated injector tube 21 having a head end 22 and a tail end 23 with a longitudinal bore 24 extending from end to end. In the present instance, the injector member 21 has a plug portion 25 at its head end which is mounted at the head end of the injector tube by a shrink wrap member 26 which covers the head end of the injector tube and includes a transverse end wall 27 which seals the head end of the bore 24 against intrusion of foreign matter. The shrink wrap member 26 includes a tear strip 28 which facilitates removal of the end cover 27 when the injector is prepared for use. A plunger 31 is mounted in the bore of the injector 21 and has a nose portion 32 adjacent the head end of the injector and is slidable in the bore and extends beyond the tail end of the bore to provide a tail piece 33. The length of the tail piece 33 is greater than the length of the head plug 25 so that in use when the tail piece is actuated to slide the plunger longitudinally towards the head end of the injector, the nose 32 of the plunger is projected beyond the head end of the bore 24. A suitable thumb rest 35 is provided on the tail end 33 of the plunger to facilitate operation of the plunger by the patient.

At the tail end, the injector tube is provided with a cover element 41 which telescopically engages over the injector tube 21 and is secured thereto by a tamper-proof sealing strip 42. Preferably, the cover element 41 is provided with a pocket clip 43 so that the injector tube may be carried in a pocket, much like a ballpoint pen or the like. In order to differentiate the device of the present invention from other devices a distinctive color is provided for the cover element and it may carry a suitable label to indicate the dosage which is packaged with the injector tube. The distinctive color of the cover element 41 is also used to differentiate between different dosages and different medications which may be packaged within the injector tube. Preferably, the tamper-proof seal 42 is the sole connection between the tube 21 and the cover 41 so that when the seal 42 is broken to separate the cover 41 from the tube 21 in preparation for use, the cover cannot be replaced, thereby indicating that the medication has been prepared for use.

The administering package of the present invention is designed to be used with a unit dose of medication which is mounted within the tubular member. The present invention contemplates that the unit dose is encapsulated in a packet permanently mounted in the injector tube so as to afford discharge of the unit dosage from the packet by operation of the plunger. The plunger discharges the unit dosage from the packet through the head end of the injector directly into the site where the medication is to be applied. In the case of medication which is taken sublingually, the plunger discharges the unit dosage into the oral cavity of the patient below the tongue. After the medication is administered, the remaining components of the medication packet and the packaging material may be discarded or recycled, as desired.

The packet of medication which includes the unit dosage is illustrated in FIGS. 3 and 4 and comprises a flat cylindrical assembly 51 comprising a support ring 52 preferably of relatively hard plastic so that the packet 51 may be retained firmly in registry with the bore 24 by the plug 25 at the head end of the tubular injector 21. The support ring 52 mounts the unit dosage of the medication, in the present instance, a tablet 53 between a pair of leaves 54 and 55 of flexible frangible material such as foil or plastic sheets. The unit dosage of medication 53 is positioned centrally between the leaves 54 and 55 of the packet 51 and the marginal area of the packet surrounding the medication 53 is sealed by conventional sealing techniques. Preferably the sealing technique not only seals the leaves 54 and 55 together about the periphery of the packet, but also seals the combination to the support ring 52 so as to provide a rigid support for the frangible leaves 54 and 55. The fabrication of the packet 51 suspends the medication 53 within the opening 56 formed in the ring 52 and this opening 56 is designed to be mounted in registry with the bore 24 of the injector 21, as shown in FIG. 5. As shown in this figure, the plug 25 bears against the underside of the mounting ring 52 to firmly anchor the packet 51 in place.

With the packet in place in registry with the bore 24, the plunger is effective to slide within the bore (through actuation of its tail portion 33) to engage the packet 51 and first provide a dispensing opening in the leaves 54 and 55 of the packet 51 and then to express the medication 53 downwardly out of the packet 51 and to direct the dosage 53 out the head end of the bore directly into the site for administration of the medication. To this end, the nose 32 of the plunger has a beveled tip 36 which cooperates with the opening 56 in the ring 52 to shear the frangible leaves 54 and 55 and thereby form the dispensing opening from which the medication may be dispensed. The beveled tip 36 is positioned at one side of the nose of the plunger to form the leading portion of the nose as the plunger is slid downwardly by pressure on the thumb rest 35 at the tail end 33.

The illustrated embodiment of the present invention is designed to facilitate the administration of vasodilator tablets sublingually in the oral cavity of the patient. However, the invention is not limited to this particular application. Other sites for administration may be indicated, e.g., the buccal cavity or the vaginal cavity. A unit dosage may consist of a thick gel which is encapsulated between two leaves of plastic film. The gel may be applied to the gum area of the oral cavity between the gum and the cheek. It will be recognized that other forms of medication, such as powders, capsules and the like may be administered directly into other body cavities. The protective sheath 26 at the head end of the injector tube may be extended to cover the entire shank of the tube and may be designed to be removed completely when used thereby assuring sterility of the head end of the tube which is injected into the body cavity.

The sublingual administration of the dosage of medication 53 is illustrated in the thumbnail sketch of FIG. 6. As shown in FIG. 6, when the dispensing package is used, the cover 41 and the tear strip 28 is removed to uncover the head end of the tube 21. The tail end of the plunger 24 is activated by the thumb rest 35 to cause the nose 32 of the plunger to project from the head end of the tube and to discharge the medication 53 into the oral cavity C of the patient P sublingually below the tongue T. The nose of the plunger guides the dose of medication directly into the desired administration site within the oral cavity.

Changes and modifications in the conformation of the elements of the device and the manner of assembly may be made without departure from the invention. Thus, the particular embodiment illustrated herein is not intended to limit the invention disclosure, but wide changes and modifications may be made therein and thereto within the scope of the following claims.

We claim:

1. A method of administering a unit dosage into a body cavity, comprising the steps of encapsulating the unit dosage in the center of a packet comprising a pair of confronting leaves of frangible material, positioning the dosage between the leaves at the center part of the packet and sealing the leaves around the periphery of the packet, to form a sealed packet which seals the unit dosage from exposure to conditions which might cause degradation of the dosage, providing an elongated tubular injector having a head end and a tail end with a longitudinal bore extending from end to end with a cross section larger than said dosage, and a plunger mounted for longitudinal displacement within said bore, said plunger having a nose portion having a cross section corresponding to the cross section of the bore, and with a beveled edge at one side of the plunger with a contour along the periphery of said nose cross section, and operable to slide within said bore, said plunger having a tail portion projecting out of said bore at the tail end of the injector, mounting said packet in said injector adjacent the head end remote from said tail end, and registering the dosage in the packet in alignment with said bore, and supporting said packet in said injector with an annular ring having a central opening corresponding in size with the cross section of said nose, said central opening having a contour conforming to the contour of said beveled edge, positioning the head end of the injector in the body cavity receiving the dosage, and dispensing said unit dosage by using the tail to displace the nose of the plunger through said packet and through the opening of said annular ring, whereby said beveled edge at one side of the plunger first penetrates the frangible material at said one side to provide a dispensing opening in the packet for the unit dosage and then the nose expresses the unit dosage out from between the leaves of the packet and through the opening of said ring and then through the head end of the injector into the body cavity receiving the dosage.

2. A method according to claim 1 wherein the dosage is to be administered by placement of the dosage under the tongue in the oral cavity of the body, said positioning step comprising placing the head end of the injector under the tongue.

3. A method according to claim 1 including the step of anchoring the leaves of said packet within the injector while expressing the dosage from therebetween.

4. A method according to claim 1 wherein said displacement of the nose of the plunger is of an extent to cause the nose of the plunger to project beyond the head end of the injector to thereby guide the dosage into a selected administration site within the body cavity.

5. A method according to claim 1 wherein said packet is supported by anchoring said leaves to said annular ring so that when said plunger penetrates the leaves to provide the dispensing opening, the penetrated leaves are retained in said injector by their being anchored to said ring.

6. A method of packaging a unit dosage for administration into a body cavity, comprising the steps of encapsulating the unit dosage in the center of a packet comprising a pair of confronting leaves of frangible material, positioning the dosage between the leaves at the center part of the packet and sealing the leaves around the periphery of the packet, to form a sealed packet which seals the unit dosage from exposure to conditions which might cause degradation of the dosage, and anchoring said packet on an annular ring having a central opening larger in size than the cross section of said dosage, with the dosage in registry with the opening, providing an elongated tubular injector having a head end and a tail end with a longitudinal bore extending between said ends with a cross section not substantially larger than as said central opening, and a plunger mounted for longitudinal displacement within said bore, said plunger having a nose portion having a cross section corresponding to the cross section of the bore, and with a beveled edge at one side of the plunger, and operable to slide within said bore and said opening, said plunger having an operator projecting out of said bore, and mounting said packet in said injector adjacent the head end remote from said tail end, and registering the dosage in the packet and said central opening in alignment with said bore, whereby upon positioning the head end of the injector in the body cavity receiving the dosage, the unit dosage may be dispensed by using the operator to displace the nose of the plunger through said packet and through the opening of said annular ring, and whereby further said beveled edge at one side of the plunger first penetrates the frangible material at said one side to provide a dispensing opening in the packet for the unit dosage and then the nose expresses the unit dosage out from between the leaves of the packet and through the opening of said ring and then through the head end of the injector into the body cavity receiving the dosage.

7. A method of packaging according to claim 6 including the step of providing a cover element for the operator which prevents use of the operator to displace the nose of the plunger, and providing a tamper-proof seal as the connection of said cover element to the injector, whereby breaking said seal is required to displace the cover element to afford use of the operator.

8. A package according to claim 6 including the step of enclosing the head end of the injector with a sterile sheath which may be removed prior to positioning the end in the body cavity.

9. A unit dosage adapted to be administered by placement into a body cavity, comprising a packet comprising a pair of confronting leaves of frangible material, a unit dosage positioned between the leaves at the center part of the packet and means sealing the leaves together around the periphery of the packet, to form a packet which seals the unit dosage from exposure to conditions which might cause degradation of the dosage, an elongated tubular injector having a head end and a tail end with a longitudinal bore extending between said ends, a plunger mounted for longitudinal displacement within said bore, said plunger having a nose portion with a beveled edge at one side of the plunger and having across section operable to slide within said bore, and a tail portion projecting out of said bore, said beveled edge having a contour extending along the periphery of the nose cross section, and an annular ring mounting said packet in said injector adjacent the head end with the dosage in alignment with said bore and supporting said packet in said injector, said annular ring having a central opening corresponding in size with the cross section of said nose and having a contour conforming to the contour of said beveled edge, the bore at the head end of the injector being open to permit communication of the bore of the injector with the cavity receiving the dosage, whereby upon displacing the nose of the plunger through said packet and through the opening of said annular ring, said beveled edge at one side of the plunger first penetrates the frangible material at said one side to provide a dispensing opening in the packet for the unit dosage and the nose then expresses the unit dosage out from between the leaves of the packet and through the opening of said ring and then through the head end of the injector into the body cavity receiving the dosage.

10. A unit dosage according to claim 9 wherein said bore extends from end to end, and said tail portion of the plunger projects from the tail end of the tubular bore of the injector a distance greater than the distance between the head end of the injector and the packet, and a cover element mounted on said tubular member to capture said tail portion and guard against inadvertent actuation of said plunger.

11. A unit dosage according to claim 10 including a tamper-proof seal securing said cover element to said tubular member, said tamper-proof seal serving as a connection between said elements which must be broken to free the tail portion for actuation of the plunger.

12. A unit dosage according to claim 10 wherein said cover element comprises an end cap having a pocket clip for anchoring the unit dosage in a pocket.

13. A unit dosage according to claim 9 including a removable sheath covering the head end of the tubular element to provide a sterile environment upon removal of the sheath prior to insertion of the head end into the body cavity.

* * * * *